(12) United States Patent
Scherich et al.

(10) Patent No.: US 12,048,826 B2
(45) Date of Patent: Jul. 30, 2024

(54) SPRING-BASED DEVICES, SYSTEMS, AND METHODS TO FACILITATE VASCULAR ACCESS

(71) Applicant: Becton, Dickinson and Company, Franklin Lakes, NJ (US)

(72) Inventors: Megan Scherich, Salt Lake City, UT (US); Jonathan Karl Burkholz, Salt Lake City, UT (US); Weston F. Harding, Lehi, UT (US); Curtis H. Blanchard, Riverton, UT (US); Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 688 days.

(21) Appl. No.: 17/192,808

(22) Filed: Mar. 4, 2021

(65) Prior Publication Data

US 2021/0290926 A1 Sep. 23, 2021

Related U.S. Application Data

(60) Provisional application No. 62/993,473, filed on Mar. 23, 2020.

(51) Int. Cl.
*A61M 39/10* (2006.01)
*A61M 25/00* (2006.01)
*A61M 25/09* (2006.01)

(52) U.S. Cl.
CPC .......... *A61M 39/10* (2013.01); *A61M 25/007* (2013.01); *A61M 25/09* (2013.01); *A61M 2039/1077* (2013.01)

(58) Field of Classification Search
CPC .... A61M 39/10; A61M 25/007; A61M 25/09; A61M 2039/1077
USPC .......................................... 604/533
See application file for complete search history.

(56) References Cited

U.S. PATENT DOCUMENTS

| 9,744,344 | B1 | 8/2017 | Devgon et al. |
| 2008/0319387 | A1* | 12/2008 | Amisar .............. A61M 25/0111 604/533 |
| 2015/0066127 | A1* | 3/2015 | Johnson ..................... A61F 2/90 623/1.11 |
| 2017/0239448 | A1* | 8/2017 | Cao ......................... A61B 10/04 |
| 2019/0021640 | A1 | 1/2019 | Burkholz et al. |
| 2019/0321590 | A1 | 10/2019 | Burkholz et al. |
| 2019/0321595 | A1 | 10/2019 | Spataro et al. |

(Continued)

FOREIGN PATENT DOCUMENTS

JP 2011167387 A 9/2011

OTHER PUBLICATIONS

Scherich, et al., Plunger-based Delivery Device to Facilitate Vascular Access, U.S. Appl. No. 17/146,400, filed Jan. 11, 2021.

*Primary Examiner* — Phillip A Gray
(74) *Attorney, Agent, or Firm* — The Webb Law Firm

(57) ABSTRACT

A catheter system may include a catheter assembly, which may include a catheter adapter. The catheter adapter may include a distal end, a proximal end, and a lumen extending through the distal end of the catheter adapter and the proximal end of the catheter adapter. The catheter assembly may include a catheter, which may extend distally from the distal end of the catheter adapter. The catheter system may include an instrument extending through a distal opening of the catheter. The instrument may include a coil spring.

20 Claims, 12 Drawing Sheets

(56) References Cited

U.S. PATENT DOCUMENTS

2020/0016374 A1    1/2020   Burkholz et al.
2020/0023166 A1    1/2020   Burkholz et al.
2020/0170559 A1    6/2020   Burkholz et al.
2020/0230353 A1    7/2020   Burkholz et al.
2020/0316346 A1   10/2020   Burkholz et al.

* cited by examiner

SPRING-BASED DEVICES, SYSTEMS, AND METHODS TO FACILITATE VASCULAR ACCESS

RELATED APPLICATIONS

This application claims the benefit of U.S. Provisional Patent Application No. 62/993,473, filed on Mar. 23, 2020, entitled "SPRING-BASED DEVICES, SYSTEMS, AND METHODS TO FACILITATE VASCULAR ACCESS," which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal or infusion using the catheter may be difficult for several reasons, particularly when a dwell time of the catheter within the vasculature is more than one day. When the catheter is left inserted in the patient for a prolonged period of time, the catheter or vein may be more susceptible to narrowing, collapse, kinking, blockage by debris (e.g., fibrin, thrombus, or platelet clots), and adhering of a tip of the catheter to the vasculature. Due to this, infusion may be unsuccessful. Also due to this, the catheter is often used for acquiring a blood sample at a time of catheter placement, but the catheter is less frequently used for acquiring a blood sample during the catheter dwell period. Therefore, when a blood sample is required, an additional needle stick is often needed to provide vein access for blood collection, which may be painful for the patient and result in higher material costs.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to spring-based devices, systems, and methods to facilitate vascular access. In some embodiments, a spring-based device or system may include an instrument, which may extend through a distal opening of a catheter. In some embodiments, the instrument may include a spring, such as, for example, a coil spring. In some embodiments, the coil spring may include a central guidewire extending there through or one or more off-center guidewires extending there through. In some embodiments, the instrument may include a tube, which may include side holes and/or a closed distal tip. In some embodiments, the instrument may include a probe or a sensor.

In some embodiments, the spring-based device or system may facilitate blood collection from a patient, fluid delivery to the patient, patient or device monitoring, or other clinical needs by utilizing an existing catheter dwelling within vasculature of the patient. In some embodiments, the spring-based device or system may reduce trauma to the vasculature, decrease blood collection time, reduce the risk of hemolysis, and overcome thrombus or fibrin sheath in or around the catheter that may prevent blood draw. In some embodiments, the spring-based device or system may be used to extend a life of the catheter dwelling within the vasculature and may reduce the number of needle sticks. In some embodiments, the spring-based device or system may include a probe.

In some embodiments, an extension set may be configured to couple to a vascular access device. In some embodiments, the extension set may include a distal connector and a proximal connector. In some embodiments, the extension set may include a housing, which may include a distal end coupled to the distal connector and a proximal end coupled to the proximal connector. In some embodiments, the extension set may include a sleeve disposed within the housing and configured to move distally such that a distal end of the sleeve is distal to the distal connector. In these embodiments, the sleeve may be configured to move distally in response to flushing of a liquid through the housing is a distal direction.

In some embodiments, a distal end of the instrument may be distal to the distal end of the sleeve. In these and other embodiments, the instrument may be coupled to the sleeve. In some embodiments, the extension set may include an instrument disposed within the sleeve. In some embodiments, the instrument may be configured to move distally such that the distal end of the instrument is distal to the distal end of the sleeve. In these embodiments, the instrument may be configured to move distally in response to flushing of the liquid through the housing in the distal direction.

In some embodiments, the distal connector may include an inner diameter. In some embodiments, an outer surface of the sleeve may include a feature. In some embodiments, the feature may include an outer diameter. In some embodiments, the outer diameter of the feature may be greater than the inner diameter of the distal connector such that the feature is prevented from moving distally through the distal connector. In some embodiments, the sleeve may include an inner diameter. In some embodiments, a proximal portion of the instrument may include an outer diameter. In some embodiments, the outer diameter of the proximal portion of the instrument may be greater than the inner diameter of the sleeve such that the proximal portion of the instrument is prevented from moving distal to the inner diameter of the sleeve.

In some embodiments, a pitch of the instrument may vary. In some embodiments, a pitch of the instrument may be uniform. In some embodiments, an outer diameter of the distal end of the instrument may be less than the outer diameter of the proximal portion of the instrument. In some embodiments, the sleeve may include a variable outer diameter. In some embodiments, the sleeve may include a tube. In some embodiments, the sleeve may include one or more side holes. In some embodiments, the sleeve may include one or more side holes and a closed distal tip.

In some embodiments, the vascular access device may include a catheter assembly. In some embodiments, a catheter system may include the catheter assembly, which may include a catheter adapter. In some embodiments, the catheter adapter may include a distal end, a proximal end, and a lumen extending through the distal end of the catheter adapter and the proximal end of the catheter adapter. In some embodiments, the catheter assembly may include the catheter, which may extend distally from the distal end of the catheter adapter. In some embodiments, the catheter may include a peripheral intravenous catheter, a peripherally-inserted central catheter, or a midline catheter.

In some embodiments, the catheter system may include the instrument, which may extend through the distal opening of the catheter. In some embodiments, a pitch of a portion of the instrument proximate the distal opening of the catheter may be less than a pitch of another portion of the instrument proximal to the distal opening of the catheter. In some embodiments, the catheter system may include a sleeve, which may extend through the instrument. In some embodiments, the sleeve may include an obturator, which may block fluid from flowing through a center of the instrument to prevent clogging of the instrument with thrombus in response to insertion of the catheter into vasculature of the patient. In these and other embodiments, an outer surface of the sleeve may contact an inner surface of the instrument along a length of the instrument to prevent fluid from flowing between the instrument and the sleeve.

In some embodiments, the catheter system may include a connector coupled to the proximal end of the catheter adapter. In some embodiments, the instrument may be coupled to the connector and may extend distally from the connector through the catheter. In some embodiments, the catheter assembly may include another extension set. In some embodiments, the catheter adapter may include a side port, which may be coupled to the other extension set. In some embodiments, the connector may be coupled to the other extension set.

In some embodiments, another instrument may extend through the distal opening of the catheter. In some embodiments, the other instrument may include another coil spring. In some embodiments, the instrument and the other instrument may be wound together such that there is limited room for thrombus to enter the catheter assembly during insertion of the catheter into the vasculature of the patient. In some embodiments, the instrument and the other instrument may be concentric and may include a central axis extending through the instrument and the other instrument. In some embodiments, the other instrument may be configured to rotate about the central axis such that a distal end of the other instrument and the distal end of the instrument are spaced apart. For example, the other instrument may be configured to rotate about the central axis and advance distally with respect to the instrument. As another example, the other instrument may be configured to rotate about the central axis and retract proximally with respect to the instrument. In some embodiments, the rotation of the other instrument about the central axis and movement of the other instrument in a distal direction or a proximal direction with respect to the instrument may open a fluid pathway through the instrument and the other instrument for blood draw.

In some embodiments, a straightener sleeve may be disposed within the catheter. In some embodiments, a sleeve may be disposed within the straightener sleeve. In some embodiments, in response to removal of a distal end of the sleeve from the straightener sleeve, the sleeve may be configured to bend into the instrument. In some embodiments, the sleeve may be configured to advance distally with respect to the straightener tube. In some embodiments, in response to the sleeve advancing distally beyond a distal end of the straightener tube, the sleeve may automatically bend into the instrument. In some embodiments, the straightener tube may be configured to retract proximally with respect to the sleeve. In some embodiments, in response to the straightener tube being retracted proximally with respect to the sleeve, the sleeve may automatically bend into the instrument. In some embodiments, the sleeve may bend into the instrument in response to heat or moisture activation.

It is to be understood that both the foregoing general description and the following detailed description are exemplary and explanatory and are not restrictive, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
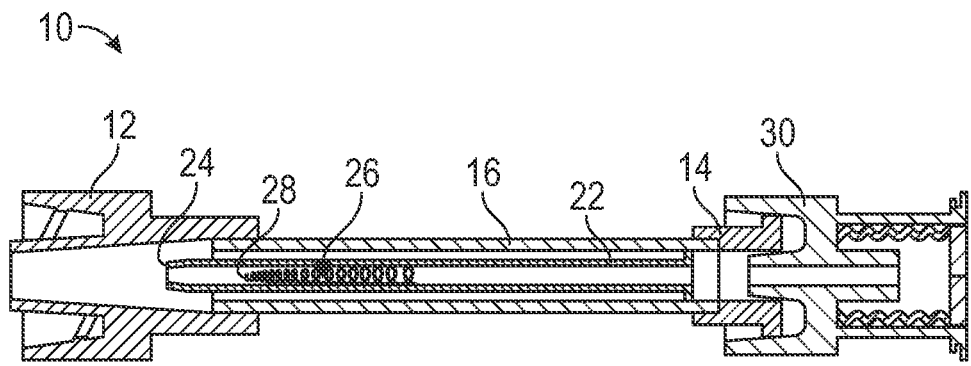
FIG. 1A is a cross-sectional view of an example extension set, according to some embodiments.
Figure 1B:
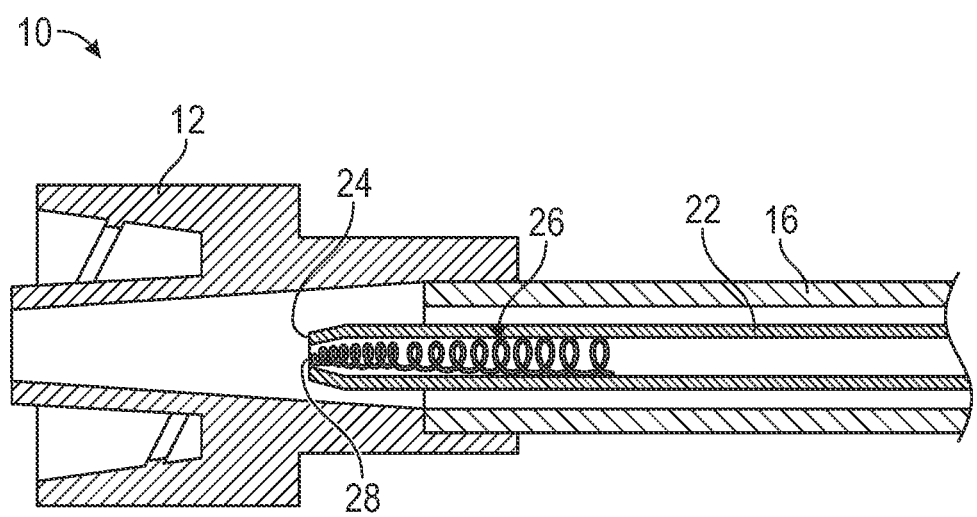
FIG. 1B is an enlarged cross-sectional view of a distal end of the extension set of FIG. 1A, according to some embodiments.

Referring now to FIGS. 1A-1B, in some embodiments, an extension set 10 may be configured to couple to a vascular access device. In some embodiments, the extension set 10 may include a distal connector 12 and a proximal connector 14. In some embodiments, the extension set 10 may include a housing 16, which may include a distal end 18 coupled to the distal connector 12 and a proximal end 20 coupled to the proximal connector 14. In some embodiments, the extension set 10 may include a sleeve 22 disposed within the housing 16 and configured to move distally such that a distal end 24 of the sleeve 22 is distal to the distal connector 12. In these embodiments, the sleeve 22 may be configured to move distally in response to flushing of a liquid or air through the housing 16 in a distal direction. In some embodiments, a vent may allow expulsion of air from the extension set 10.

In some embodiments, the sleeve 22 may include a tube, which may include an open distal end, as illustrated, for example, in FIGS. 1A-1B. In some embodiments, the sleeve 22 may include the tube, which may include side holes and/or a closed distal tip. In some embodiments, the sleeve 22 may include a probe or a sensor. In some embodiments, the extension set 10 may include an instrument 26 disposed within the sleeve 22. In some embodiments, the instrument 26 may include a spring, such as, for example, a coil spring. In some embodiments, the coil spring may be constructed of metal or another suitable material. In some embodiments, the coil spring may include a central guidewire extending there through or one or more off-center guidewires extending there through. In some embodiments, the instrument 26 may include a tube, which may include side holes and/or a closed distal tip. In some embodiments, the instrument 26 may include a probe or a sensor.

In some embodiments, the instrument 26 may be configured to move distally such that a distal end 28 of the instrument 26 is distal to the distal end 24 of the sleeve 22. In these embodiments, the instrument 26 may be configured to move distally in response to flushing of the liquid through the housing 16 in the distal direction. In some embodiments, the proximal connector 14 may be coupled to a needleless connector 30.

Figure 1C:
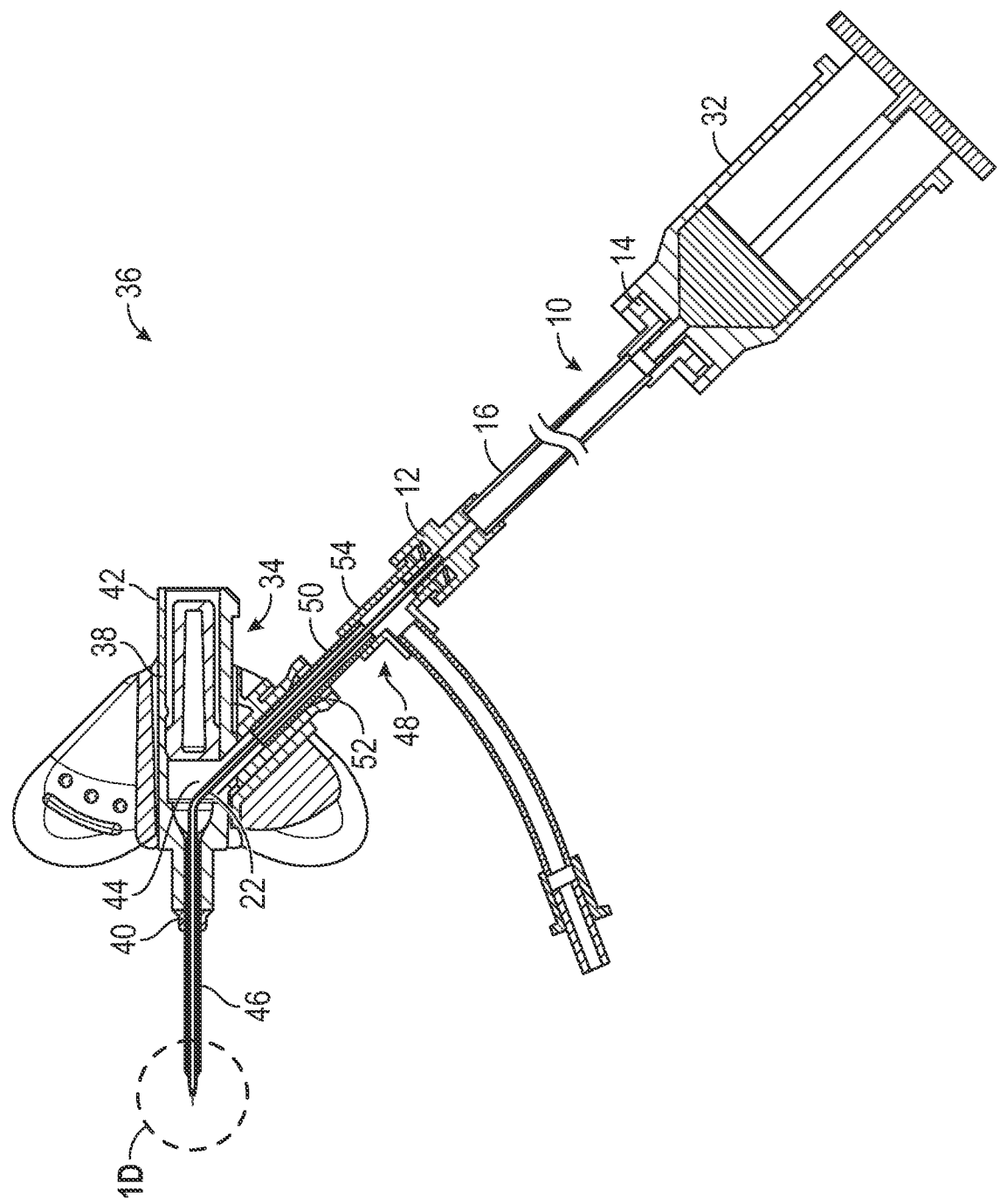
FIG. 1C is a cross-sectional view of an example catheter system, illustrating an example sleeve and an example instrument of the extension set of FIG. 1A in a distal position in response to flushing of a liquid through the housing in a distal direction, according to some embodiments.

Referring now to FIG. 1C, in some embodiments, an infusion device 32, such as, for example, a syringe, may be coupled to the proximal connector 14. In some embodiments, the infusion device 32 may be directly coupled to the proximal connector 14. In other embodiments, the needleless connector 30 may be disposed between the infusion device 32 and the proximal connector 14. In some embodiments, the needleless connector 30 may be coupled to the infusion device 32. In some embodiments, the infusion device 32 may be activated (such as, for example, a plunger of the syringe being depressed) to flush the liquid within the infusion device 32 through the housing 16 in the distal direction and/or a catheter assembly 34 coupled to the distal connector 12.

In some embodiments, a catheter system 36 may include the catheter assembly 34 and the extension set 10. In some embodiments, the catheter assembly 34 may include a catheter adapter 38. In some embodiments, the catheter adapter 38 may include a distal end 40, a proximal end 42, and a lumen 44 extending through the distal end 40 of the catheter adapter 38 and the proximal end 42 of the catheter adapter 38. In some embodiments, the catheter assembly 34 may include the catheter 46, which may extend distally from the distal end 40 of the catheter adapter 38. In some embodiments, the catheter 46 may include a peripheral intravenous catheter, a peripherally-inserted central catheter, or a midline catheter.

In some embodiments, the catheter assembly 34 may include another extension set 48, which may be integrated with the catheter adapter 38. In some embodiments, the other extension set 48 may include an extension tube 50, which may be integrated with a side port 52 of the catheter adapter 38 disposed between the distal end 40 and the proximal end 42. In some embodiments, an adapter 54 may be coupled to a proximal end of the extension tube 50. In some embodiments, the distal connector 12 may be coupled to the adapter 54. In some embodiments, the distal connector 12 may be coupled to the proximal end 20 of the catheter adapter 38, and the sleeve 22 may be disposed in generally straight line within the catheter adapter 38.

Figure 1D:
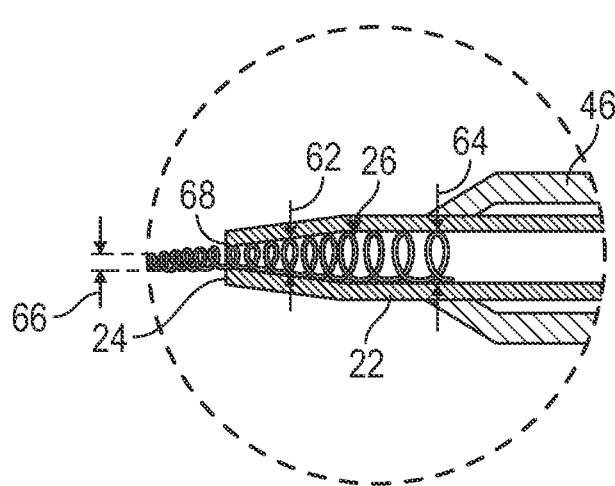
FIG. 1D is an enlarged cross-sectional view of a distal end of the catheter system of FIG. 1C, illustrating the sleeve and the instrument in the distal position, according to some embodiments.
Figure 1E:
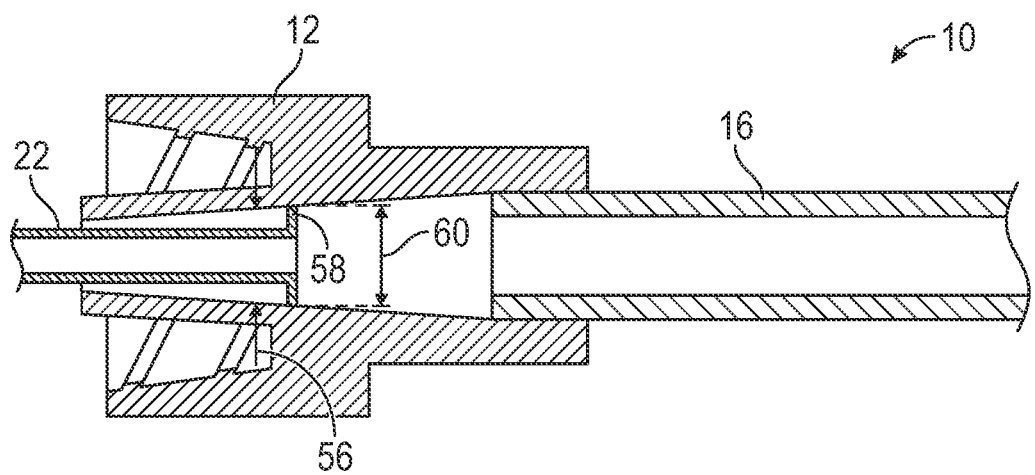
FIG. 1E is an enlarged cross-section of a portion of the catheter system of FIG. 1C, illustrating the sleeve in the distal position and an example feature on an outer surface of the sleeve, according to some embodiments.

Referring now to FIGS. 1D-1E, in some embodiments, the distal connector 12 and/or the housing 16 may include an inner diameter 56. In some embodiments, the housing 16 may be rigid, semi-rigid, or flexible. In some embodiments, an outer surface of the sleeve 22 may include a feature 58. In some embodiments, the feature 58 may be integrated or monolithically formed as a single unit with the sleeve 22. In some embodiments, the feature 58 may be a separate component from the sleeve 22 and coupled to the sleeve 22. In some embodiments, the feature 58 may be wedge-shaped or another suitable shape. In some embodiments, the sleeve 22 may be retracted using a retraction mechanism that pinches down on the sleeve 22 and the feature 58. In some embodiments, the retraction mechanism may be disposed on the housing 16. The retraction mechanism may be further described in U.S. patent application Ser. No. 17/146,400, entitled "PLUNGER-BASED DELIVERY DEVICE TO FACILITATE VASCULAR ACCESS," filed Jan. 11, 2021, which is hereby incorporated by reference in its entirety.

In some embodiments, the feature 58 may include an outer diameter 60. In some embodiments, the outer diameter 60 of the feature 58 may be greater than the inner diameter 56 such that the feature 58 is prevented from moving distally through the distal connector 12. In some embodiments, the sleeve 22 may include an inner diameter 62. In some embodiments, a proximal portion of the instrument 26 may include an outer diameter 64. In some embodiments, the outer diameter 64 of the proximal portion of the instrument 26 may be greater than the inner diameter 62 of the sleeve 22 such that the proximal portion of the instrument 26 is prevented from moving distal to the inner diameter 62 of the sleeve 22.

In some embodiments, in response to activating the infusion device 32 or flushing, the sleeve 22 and the instrument 26 may be moved from a proximal position to a distal position, illustrated, for example, in FIGS. 1D-1E. In some embodiments, in response to the sleeve 22 and the instrument 26 being in the distal position, the sleeve 22 may be wedged within the distal connector 12 in an interference fit due to the outer diameter 60 being greater than the inner diameter 56 and/or the instrument 26 may be wedged within the distal end 24 of the sleeve 22 in an interference fit due to the outer diameter 64 being greater than the inner diameter 62. In some embodiments, in response to the sleeve 22 and the instrument 26 being in the distal position, the sleeve 22 and the instrument 26 may extend distal to a distal end 65 of the catheter 46. In some embodiments, the distal end 28 of the instrument 26 may be between 0 and about 80 mm beyond the distal end of the catheter 46. In some embodiments, the distal end 28 of the instrument 26 may be greater than 80 mm beyond the distal end of the catheter 46. In some embodiments, an outer diameter 66 of the distal end 28 of the instrument 26 may be less than the outer diameter 64 of the proximal portion of the instrument 26.

Referring now to FIGS. 1C-1E, in some embodiments, the instrument 26 may create a fluid path for blood to flow into the catheter 46 and the catheter assembly 34. In some embodiments, the infusion device 32 may also act as a blood collection device (such as, for example, by retracting the plunger) or any other suitable blood collection device (such as, for example, a VACUTAINER® or a VACUTAINER® LUER-LOK™, available from Becton Dickinson and Company of Franklin Lakes, New Jersey) may be coupled to the extension set 10 to collect blood from the patient. In some embodiments, the sleeve 22 may be soft, which may decrease a likelihood of the sleeve 22 damaging the vasculature. In some embodiments, a durometer of the sleeve 22 may be less than a durometer of the catheter 46. In some embodiments, the sleeve 22 creates an isolated or closed fluid path for blood flow and reduces a risk of contamination of the blood due to drug adsorption in the catheter assembly 34. In some embodiments, the catheter 46 may serve as the fluid path in addition or as an alternative to the sleeve 22. In some embodiments, the sleeve 22 may extend through the catheter 46 and the catheter adapter 38.

In some embodiments, a pitch of the instrument 26 may vary. In some embodiments, the instrument 26 may include a tight pitch proximate a distal opening 68 of the sleeve 22 and/or adjacent the distal end of the catheter 46. In some embodiments, the tight pitch may block obstruction from fibrin sheath, thrombus, or a vein wall under vacuum pressure when the blood collection device is activated. In some embodiments, the tight pitch may prevent collapse of the catheter 46 under vacuum pressure when the blood collection device is activated. In some embodiments, a pitch of the instrument 26 may be uniform. In some embodiments, the instrument 26 may include a more open pitch proximal to the tight pitch, which may facilitate blood flow and an increased blood flow rate in comparison to a closed sleeve or the tight pitch.

In some embodiments, the instrument 26 may be coupled to a guidewire (not illustrated), which may extend through the instrument 26. In some embodiments, the distal end 28 of the instrument 26 may be rounded or bent, which may prevent trauma to the vein wall.

Referring now to FIGS. 2A-2D, an extension set 70 is illustrated, according to some embodiments. In some embodiments, the extension set 70 may be similar or identical to the extension set 10 in terms of one or more features and/or operation. In some embodiments, the distal end 28 of the instrument 26 may be distal to the distal end 24 of the sleeve 22. In these and other embodiments, the instrument 26 may be coupled to the sleeve 22. In some embodiments, the instrument 26 may be coupled to the sleeve 22 in any suitable way, such as by embedding, bonding, weld, adhesive, a solvent, an interference fit, etc. In some embodiments, the instrument 26 may be wedged within the distal end 24 of the sleeve 22 in an interference fit due to the outer diameter 64 being greater than the inner diameter 62. In some embodiments, the instrument 26 may be wedged within the distal end 24 of the sleeve 22 in the interference fit without flushing. In some embodiments, a guidewire (see, for example, the guidewire 84 of FIGS. 6A-6B or the guidewire 84 of FIGS. 4A-4C) may be coupled to and/or may extend through the instrument 26.

Figure 2A:
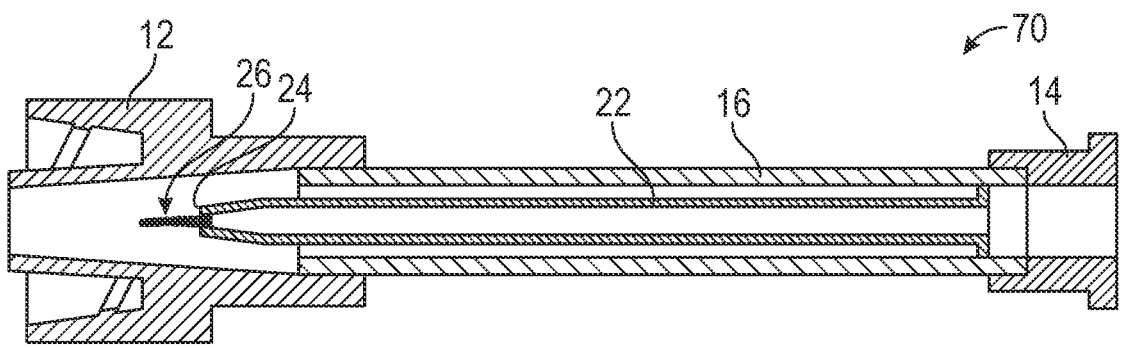
FIG. 2A is a cross-sectional view of another extension set, according to some embodiments.
Figure 2B:
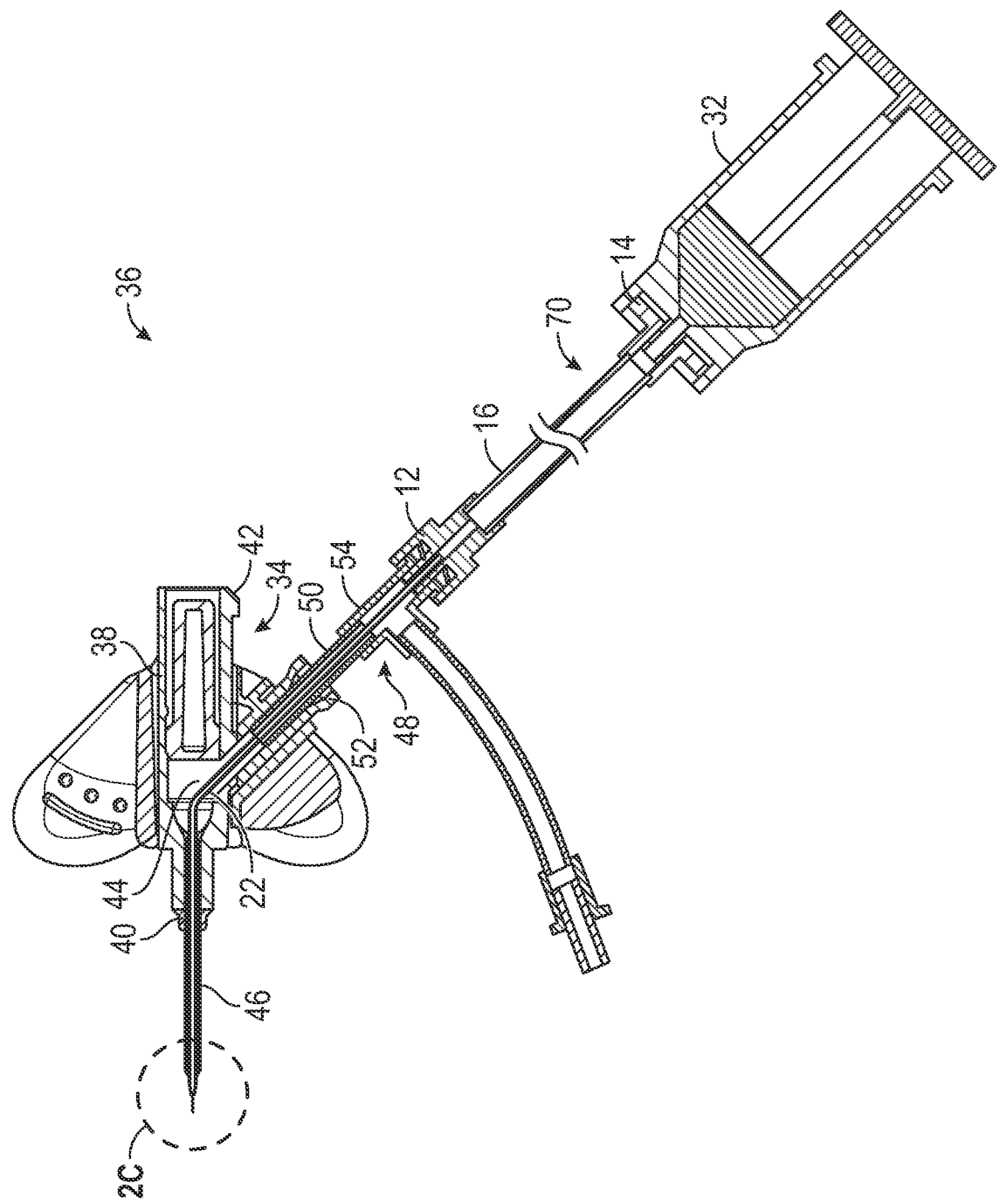
FIG. 2B is a cross-sectional view of an example catheter system, illustrating an example sleeve and an example instrument of the extension set of FIG. 2A in the distal position in response to flushing of the liquid through the housing in the distal direction, according to some embodiments.
Figure 2C:
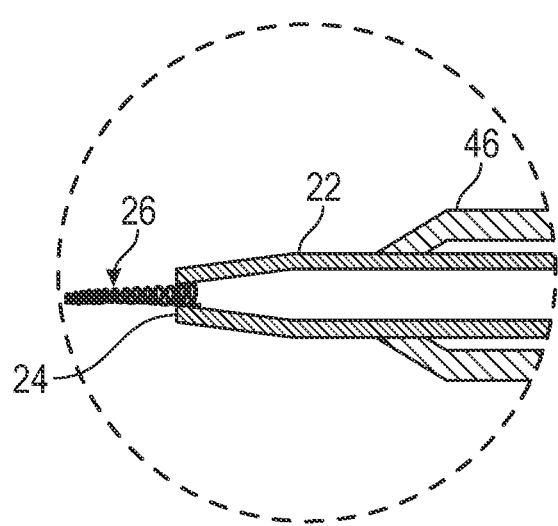
FIG. 2C is an enlarged cross-sectional view of a distal end of the catheter system of FIG. 2B, illustrating the sleeve and the instrument in the distal position, according to some embodiments.
Figure 2D:
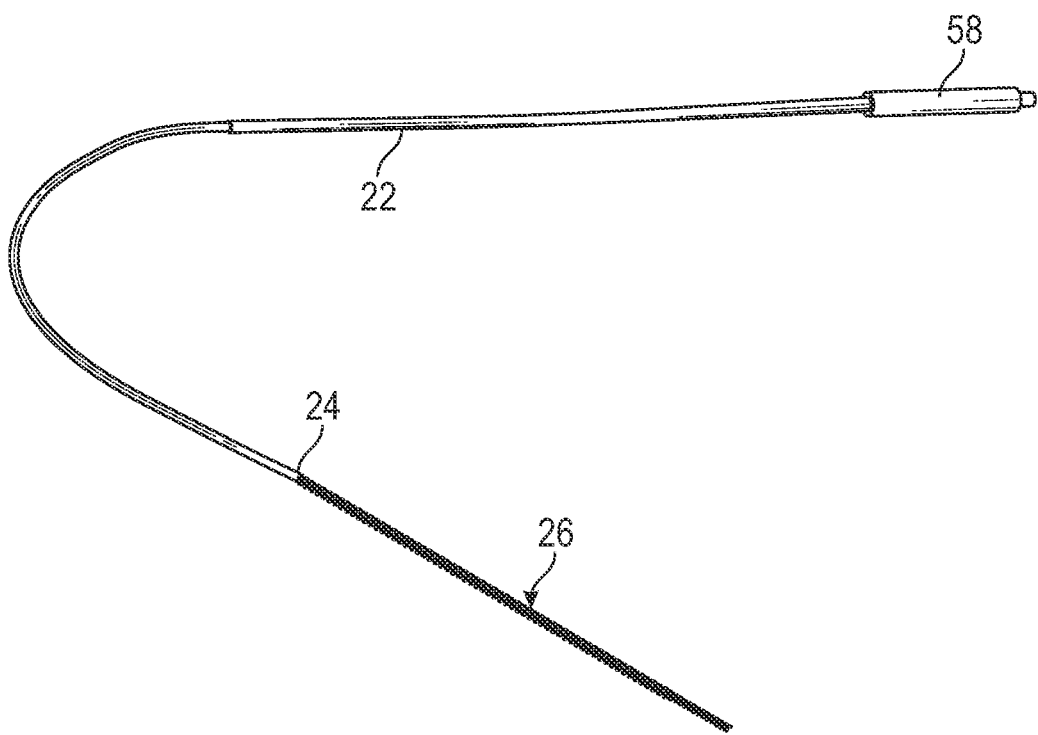
FIG. 2D is an upper perspective view of another example sleeve and another example instrument, according to some embodiments.

As illustrated in FIG. 2D, in some embodiments, the sleeve 22 may include a variable outer diameter and a corresponding variable inner diameter. In some embodiments, the variable outer diameter and the corresponding variable inner diameter may facilitate greater blood flow through the sleeve 22 in response to the sleeve 22 being in the distal position. In some embodiments, the outer diameter of the sleeve 22 may increase in response to a diameter of an internal geometry of the catheter assembly 34 increasing. In some embodiments, the instrument 26 may include two tight pitch sections and a more open pitch section between the two tight pitch sections.

Figure 6A:
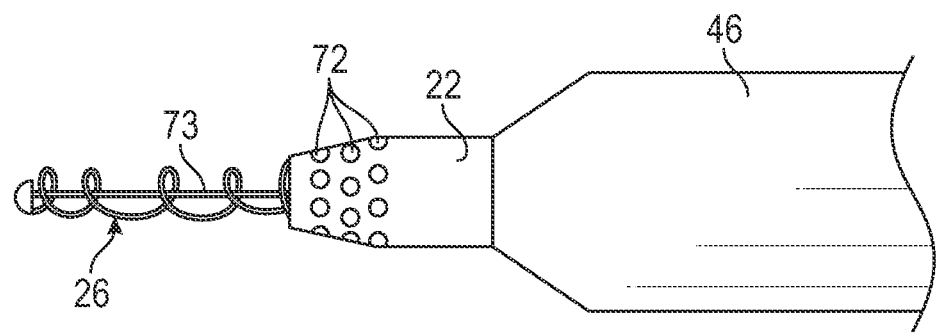
FIG. 6A is an upper perspective view of a distal end of another example catheter system, according to some embodiments.
Figure 6B:
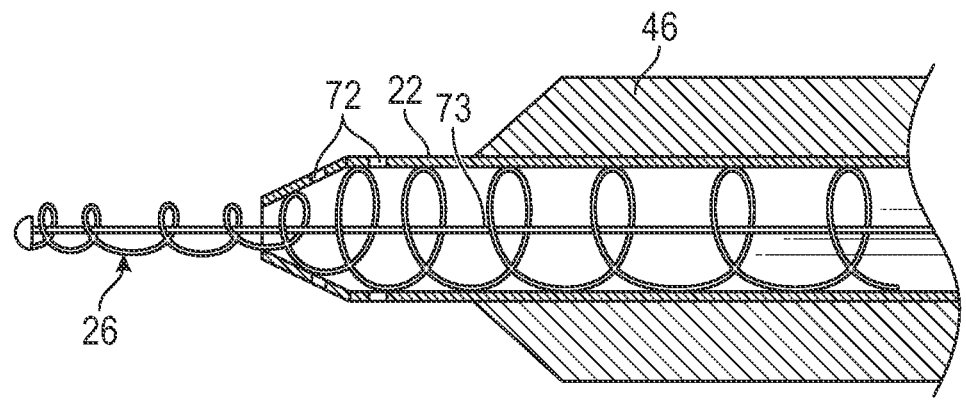
FIG. 6B is a cross-sectional view of the distal end of the catheter system of FIG. 6A, according to some embodiments.

Referring now to FIGS. 6A-6B, in some embodiments, the sleeve 22 may include one or more side holes 72, which may facilitate a fluid path for blood draw. In some embodiments, a guidewire 84 may extend through the instrument 26 and provide stiffening to reduce a likelihood of collapse of the catheter 46. As mentioned, in some embodiments, the distal end 28 of the instrument 26 may be rounded or bent, which may prevent trauma to the vein wall. In some embodiments, the instrument 26 and/or the sleeve 22 may include staged deployment, which may be further described, for example, in U.S. patent application Ser. No. 16/037,246, filed Jul. 17, 2018, entitled "EXTENSION HOUSING A SLEEVE OR INTRAVENOUS CATHETER," U.S. patent application Ser. No. 16/388,650, filed Apr. 18, 2019, entitled "INSTRUMENT DELIVERY DEVICE HAVING A ROTARY ELEMENT," U.S. patent application Ser. No. 16/037,319, filed Jul. 17, 2018, entitled "MULTI-DIAM- ETER CATHETER AND RELATED DEVICES AND METHODS," U.S. patent application Ser. No. 16/502,541, filed Jul. 3, 2019, entitled "DELIVERY DEVICE FOR A VASCULAR ACCESS INSTRUMENT," U.S. patent application Ser. No. 16/691,217, filed Nov. 21, 2019, entitled "SYRINGE-BASED DELIVERY DEVICE FOR A VASCULAR ACCESS INSTRUMENT," U.S. patent application Ser. No. 16/742,013, filed Jan. 14, 2020, entitled "CATHETER DELIVERY DEVICE AND RELATED SYSTEMS AND METHODS," and U.S. patent application Ser. No. 16/838,831, filed Apr. 2, 2020, entitled "VASCULAR ACCESS INSTRUMENT HAVING A FLUID PERMEABLE STRUCTURE, AND RELATED DEVICES AND METHODS," which are each incorporated by reference in their entirety.

Figure 3A:
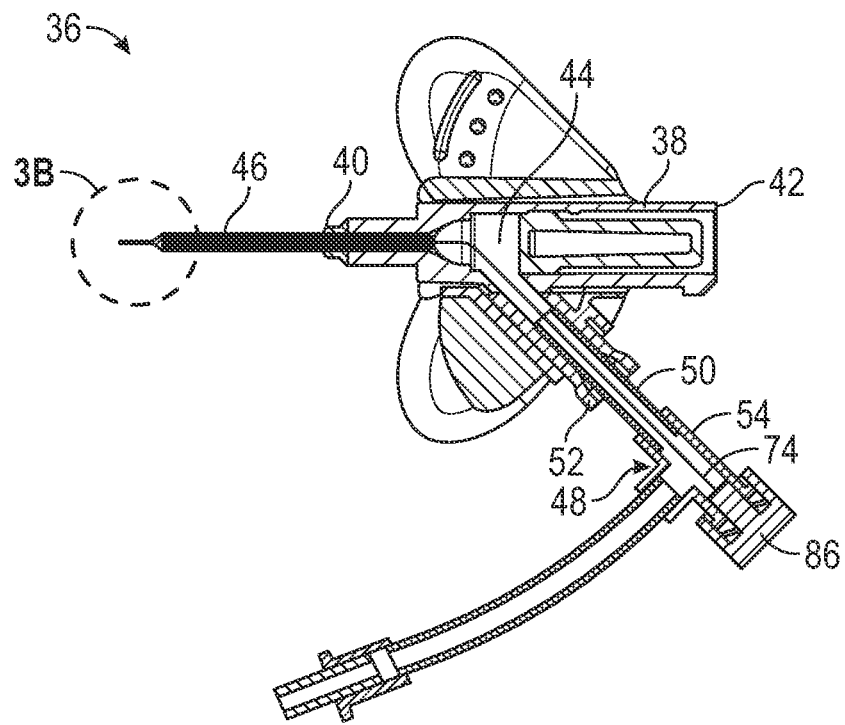
FIG. 3A is a cross-sectional view of another example catheter system, illustrating an example heat-activated or moisture-activated guidewire, according to some embodiments.
Figure 3B:
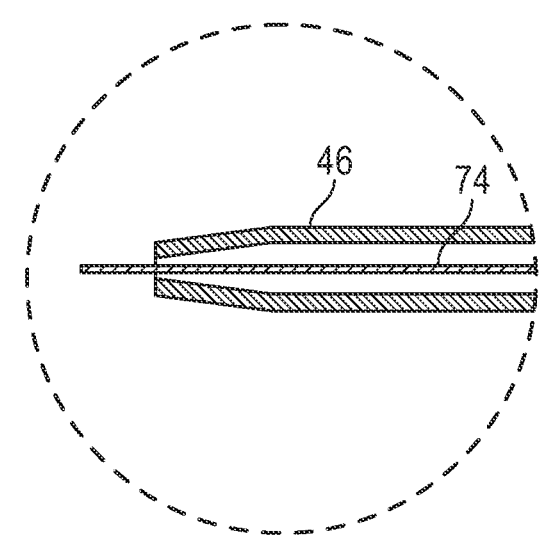
FIG. 3B is a cross-sectional view of a distal end of the catheter system of FIG. 3A, illustrating the heat-activated or moisture-activated guidewire prior to heat or moisture activation.
Figure 3C:
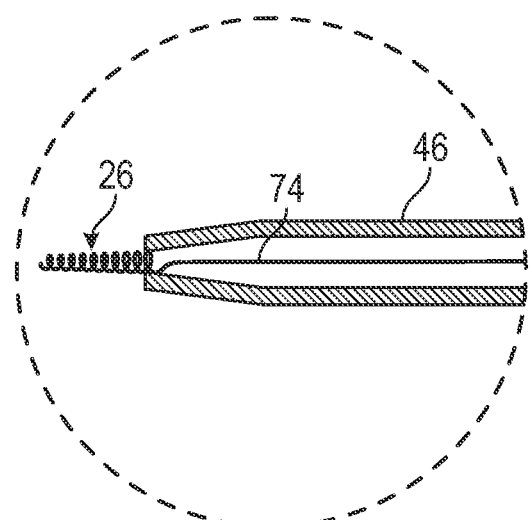
FIG. 3C is a cross-sectional view of the distal end of the catheter system of FIG. 3A, illustrating the heat-activated or moisture-activated guidewire after heat or moisture activation.

Referring back to FIGS. 3A-3C, in some embodiments, the catheter system 36 may include a particular guidewire 74, which may bend to form the instrument 26 in response to activation by heat or moisture. FIG. 3B is a cross-sectional view of a distal end of the catheter system of FIG. 3A, illustrating the heat-activated or moisture-activated guidewire prior to heat or moisture activation, according to some embodiments. In some embodiments, the guidewire 74 may be inserted through the catheter assembly 34 to reduce obstruction from fibrin sheath or thrombus. In some embodiments, the guidewire 74 and/or the instrument 26 may be constructed of a shape-memory polymer or alloy.

Figure 3D:
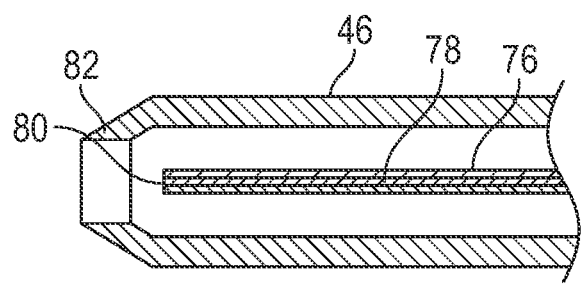
FIG. 3D is a cross-sectional view of an example straightener sleeve and example guidewire, according to some embodiments.
Figure 3E:
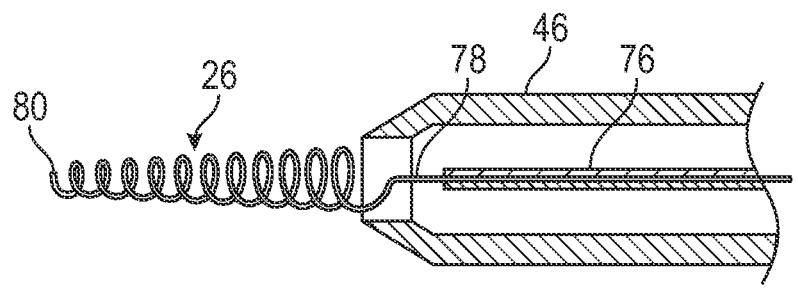
FIG. 3E is a cross-sectional view of the guidewire of FIG. 3D advanced distally or the straightener sleeve of FIG. 3D retracted, according to some embodiments.

Referring now to FIGS. 3D-3E, in some embodiments, a straightener sleeve 76 may be disposed within the catheter 46. In some embodiments, a guidewire 78 may be disposed within the straightener sleeve 76, which may extend through the catheter assembly 34. In some embodiments, in response to removal of a distal end 80 of the guidewire 78 from the straightener sleeve 76, the guidewire 78 may be configured to bend into the instrument 26. In some embodiments, the guidewire 78 may be configured to advance distally with respect to the straightener sleeve 76 for blood draw. In some embodiments, in response to the guidewire 78 advancing distally beyond a distal end of the straightener sleeve 76, the guidewire 78 may automatically bend into the instrument. In some embodiments, the straightener sleeve 76 may be configured to retract proximally with respect to the guidewire 78 for blood draw. In some embodiments, in response to the straightener sleeve 76 being retracted proximally with respect to the guidewire 78, the guidewire 78 may automatically bend into the instrument 26.

Figure 4A:
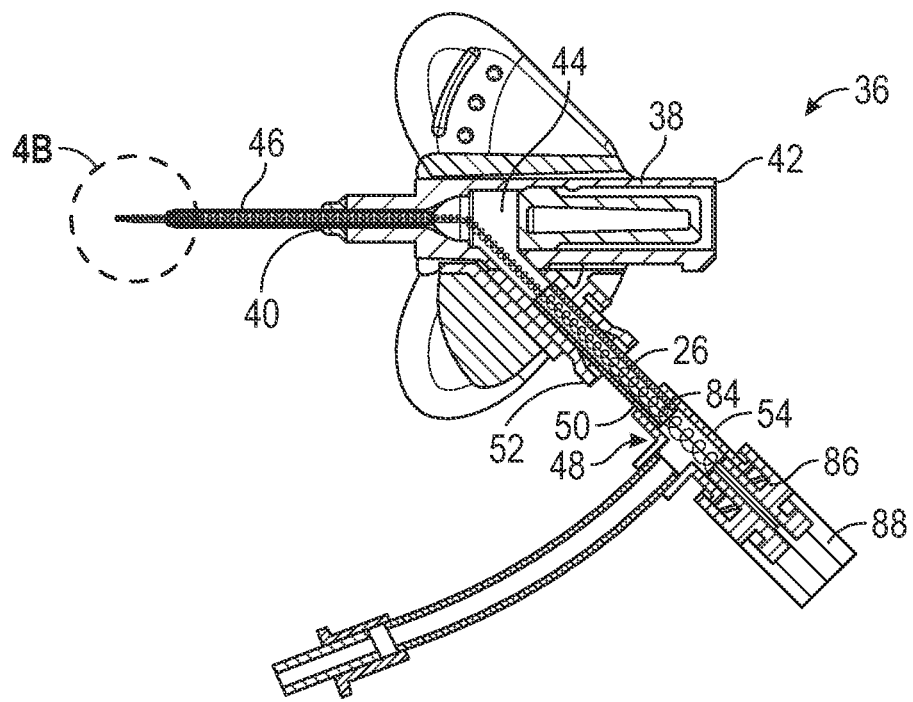
FIG. 4A is a cross-sectional view of another example catheter system, according to some embodiments.
Figure 4B:
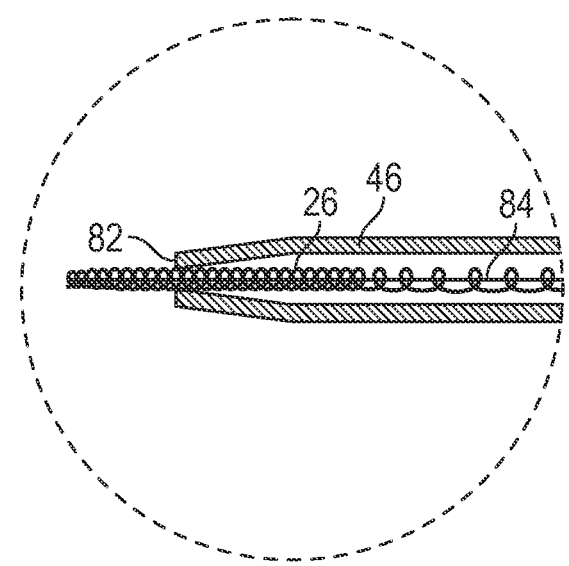
FIG. 4B is an enlarged cross-sectional view of a distal end of the catheter system of FIG. 4A, according to some embodiments.
Figure 4C:
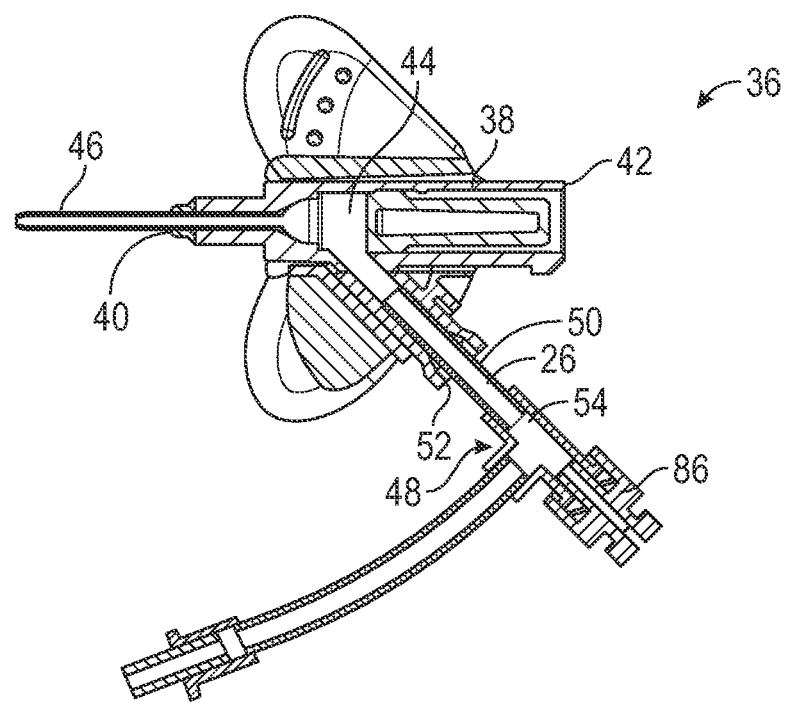
FIG. 4C is a cross-sectional view of the catheter system of FIG. 4A, illustrating an example guidewire removed from the catheter system, according to some embodiments.

Referring now to FIGS. 4A-4C, in some embodiments, the catheter system 36 may include the instrument 26, which may extend through the distal opening 82 of the catheter 46. In some embodiments, a pitch of a portion of the instrument 26 proximate the distal opening 82 of the catheter 46 may be less than a pitch of another portion of the instrument 26 proximal to the distal opening 82 of the catheter 46. In some embodiments, the catheter system 36 may include a guidewire 84, which may extend through the instrument 26. In some embodiments, the guidewire 84 may include an obstruction such as a rounded nose, which may block fluid from flowing through a center of the instrument 26 to prevent clogging of the instrument 26 with thrombus in response to insertion of the catheter 46 into vasculature of the patient. In these and other embodiments, an outer surface of the guidewire 84 may contact an inner surface of the instrument 26 all or a portion of a length of the instrument 26 to prevent fluid from flowing between the instrument 26 and the guidewire 84.

In some embodiments, the catheter system 36 may include a connector 86 coupled to the catheter assembly 34. For example, the connector 86 may be coupled to the adapter 54 or the proximal end 42 of the catheter adapter 38. In some embodiments, the instrument 26 may be coupled to the connector 86 and may extend distally from the connector 86 through the catheter 46. In some embodiments, the guidewire 84 may be coupled to another connector 88, which may be coupled to the connector 86. In some embodiments, the guidewire 84 may be removable from the catheter system 36. In some embodiments, the guidewire 84 may be removed from the catheter system 36 for blood draw or infusion.

Figure 5A:
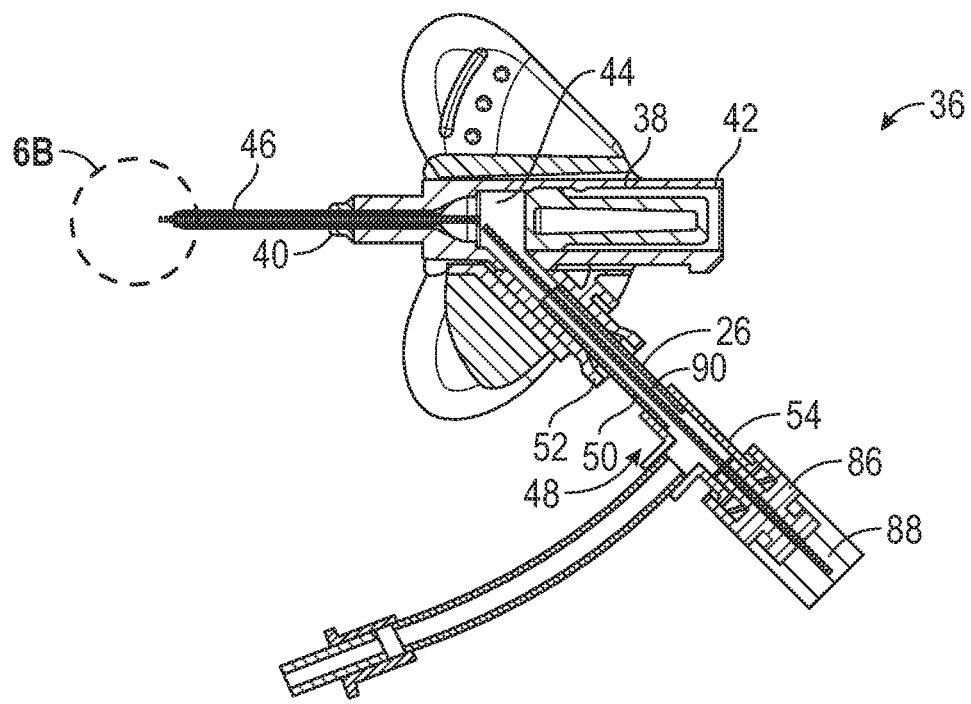
FIG. 5A is a cross-sectional view of another catheter system, according to some embodiments.
Figure 5B:
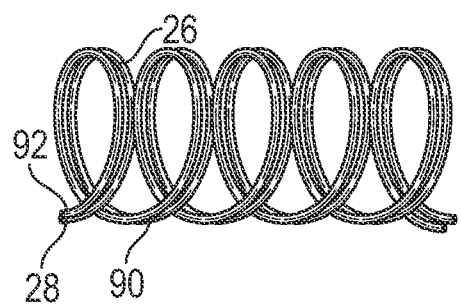
FIG. 5B is an enlarged view of a portion of an instrument and a portion of another instrument.
Figure 5C:
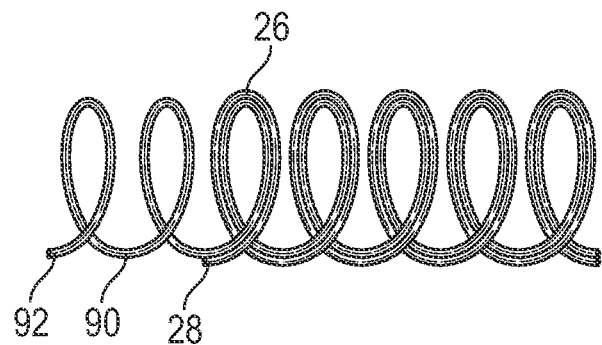
FIG. 5C is an enlarged view of the other instrument advanced distally with respect to the instrument, according to some embodiments.

Referring now to FIGS. 5A-5C, in some embodiments, another instrument 90 may extend through the distal opening 82 of the catheter 46. In some embodiments, the instrument 26 and the other instrument 90 may be wound together such that there is limited room for thrombus or other obstructions to enter the catheter assembly 34 during insertion of the catheter 46 into the vasculature of the patient. In some embodiments, the instrument 26 and the other instrument 90 may be concentric and may include a central axis extending through the instrument 26 and the other instrument 90.

In some embodiments, the other instrument 26 may be configured to rotate about the central axis such that a distal end 92 of the other instrument 90 and the distal end 28 of the instrument 26 are spaced apart. For example, the other instrument 90 may be configured to rotate about the central axis and advance distally with respect to the instrument 26. In some embodiments, the instrument 26 and the other instrument 90 may be nested together such that they contact each other and one is wound with respect to the other. As another example, the other instrument 90 may be configured to rotate about the central axis and retract proximally with respect to the instrument 26. In some embodiments, the rotation of the other instrument 90 about the central axis and movement of the other instrument 90 in a distal direction or a proximal direction with respect to the instrument 26 may open a fluid pathway through the instrument 26 and the other instrument 90 for blood draw or infusion, as illustrated, for example, in FIG. 5C.

Figure 7A:
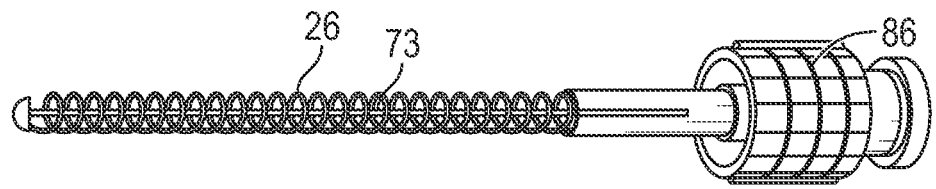
FIG. 7A is an upper perspective view of an example device configured to extend through a catheter, according to some embodiments.
Figure 7B:
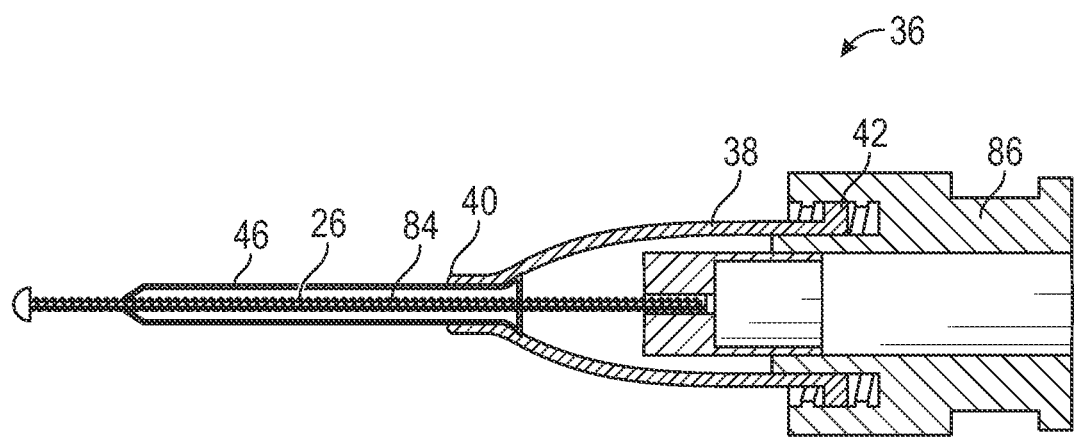
FIG. 7B is a cross-sectional view of the device of FIG. 7A coupled to another example catheter system, according to some embodiments.

Referring now to FIGS. 7A-7B, in some embodiments, the connector 86 may be coupled to the proximal end 42 of the catheter adapter 38. In some embodiments, the instrument 26 may be coupled to the connector 86 and may extend distally from the connector 86 in a generally straight line through the catheter 46. In some embodiments, the instrument 26 may include the coil spring. In some embodiments, the coil spring may include a central guidewire extending there through or one or more off-center guidewires extending there through. In some embodiments, the instrument 26 may include a tube, which may include side holes and/or a closed distal tip. In some embodiments, the instrument 26 may include a probe or a sensor.

All examples and conditional language recited herein are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. An extension set to couple to a vascular access device, the extension set comprising:
a distal connector;
a proximal connector;

a housing, comprising a distal end coupled to the distal connector and a proximal end coupled to the proximal connector;

a tube disposed within the housing and configured to move distally such that a distal end of the tube is distal to the distal connector; and a coil spring bonded to and disposed within the tube, wherein a distal end of the coil spring is distal to the distal end of the tube or the coil spring is configured to move distally such that the distal end of the coil spring is distal to the distal end of the tube.

2. The extension set of claim 1, wherein the distal end of the coil spring is distal to the distal end of the tube.

3. The extension set of claim 1, wherein the coil spring is configured to move distally such that the distal end of the coil spring is distal to the distal end of the tube.

4. The extension set of claim 1, wherein the distal connector comprises an inner diameter, wherein an outer surface of the tube comprises a feature, wherein the feature comprises an outer diameter, wherein the outer diameter of the feature is greater than the inner diameter such that the feature is prevented from moving distally through the distal connector.

5. The extension set of claim 1, wherein the coil spring is configured to move distally such the distal end of the coil spring is distal to the distal end of the tube, wherein the tube comprises an inner diameter, wherein a proximal portion of the coil spring comprises an outer diameter, wherein the outer diameter is greater than the inner diameter such that the proximal portion of the coil spring is prevented moving distal to the inner diameter of the tube.

6. The extension set of claim 1, wherein a pitch of the coil spring varies.

7. The extension set of claim 1, wherein a pitch of the coil spring is uniform.

8. The extension set of claim 1, wherein an outer diameter of the distal end of the coil spring is less than an outer diameter of a proximal portion of the coil spring.

9. The extension set of claim 1, wherein the tube has a variable outer diameter.

10. The extension set of claim 1, wherein the tube comprises a plurality of side holes.

11. A catheter system, comprising:
a catheter assembly, comprising:
a catheter adapter, comprising a distal end, a proximal end, and a lumen extending through the distal end and the proximal end; and
a catheter extending distally from the distal end of the catheter adapter; and a coil spring bonded to the catheter and extending through a distal opening of the catheter.

12. The catheter assembly of claim 11, wherein a pitch of the coil spring proximate a distal opening of the catheter is less than a pitch of the coil spring proximal to the distal opening of the catheter.

13. The catheter system of claim 11, further comprising a guidewire extending through the coil spring.

14. The catheter assembly of claim 13, wherein the guidewire includes an obturator, wherein an outer surface of the obturator contacts an inner surface of the coil spring along a length of the coil spring.

15. The catheter system of claim 11, further comprising another coil spring extending through the distal opening of the catheter, wherein the other coil spring is configured to rotate and advance distally with respect to the coil spring.

16. The catheter system of claim 11, further comprising a connector coupled to the proximal end of the catheter adapter, wherein the coil spring is coupled to the connector and extends distally from the connector through the catheter.

17. The catheter system of claim 11, wherein the catheter assembly further comprises an extension set, wherein the catheter adapter further comprises a side port coupled to the extension set, further comprising a connector coupled to the extension set, wherein the coil spring is coupled to the connector and extends distally from the connector through the catheter.

18. A catheter system, comprising:
a catheter assembly, comprising:
a catheter adapter, comprising a distal end, a proximal end, and a lumen extending through the distal end and the proximal end; and
a catheter extending distally from the distal end of the catheter adapter;
a straightener tube disposed within the catheter; and
a guidewire bonded to and disposed within the straightener tube, wherein in response to removal of a distal end of the guidewire from the straightener tube, the guidewire automatically bends into a coil spring.

19. The catheter system of claim 18, wherein the guidewire is configured to advance distally with respect to the straightener tube, wherein in response to the guidewire advancing distally beyond a distal end of the straightener tube, the guidewire automatically bends into the coil spring.

20. The catheter system of claim 18, wherein the straightener tube is configured to retract proximally with respect to the guidewire, wherein in response to the straightener tube being retracted proximally with respect to the guidewire, the guidewire is configured to bend into the coil spring.

* * * * *